United States Patent [19]

Haugk et al.

[11] Patent Number: 5,646,100
[45] Date of Patent: Jul. 8, 1997

[54] MILD, AQUEOUS SKIN CLEANSING COMPOSITION

[75] Inventors: Peter D. Haugk, Lincoln Park; Teresa Pavlak, Fanwood; Laura Briceno, Perth Amboy, all of N.J.

[73] Assignee: Colgate-Palmolive Company, New York, N.Y.

[21] Appl. No.: 386,399

[22] Filed: Feb. 10, 1995

Related U.S. Application Data

[63] Continuation-in-part of Ser. No. 195,235, Feb. 14, 1994, abandoned.

[51] Int. Cl.$^6$ .................. C11D 1/29; C11D 1/90; C11D 1/94; C11D 3/48
[52] U.S. Cl. .................. 510/131; 510/132; 510/138; 510/427; 510/470; 510/501; 510/506; 510/495
[58] Field of Search .................. 252/106, 546, 252/551, 174.17, 174.23, DIG. 2, DIG. 5; 510/131, 132, 427, 495, 501, 506, 138, 470

[56] References Cited

U.S. PATENT DOCUMENTS

| | | | |
|---|---|---|---|
| 4,657,999 | 4/1987 | Hoefer et al. | 526/200 |
| 4,764,365 | 8/1988 | Boothe et al. | 424/81 |
| 4,839,098 | 6/1989 | Wisotzki et al. | 252/557 |
| 4,963,535 | 10/1990 | Sebag et al. | 514/54 |
| 5,139,781 | 8/1992 | Birtwistle et al. | 424/401 |
| 5,147,574 | 9/1992 | MacGilp et al. | 252/108 |
| 5,158,699 | 10/1992 | MacGilp et al. | 252/132 |
| 5,234,618 | 8/1993 | Kamegai et al. | 252/106 |
| 5,284,603 | 2/1994 | Repinec, Jr. et al. | 252/546 |
| 5,296,157 | 3/1994 | MacGilp et al. | 252/108 |
| 5,296,158 | 3/1994 | MacGilp et al. | 252/108 |
| 5,330,674 | 7/1994 | Urfer et al. | 252/176.17 |
| 5,385,696 | 1/1995 | Repinec, Jr. et al. | 252/546 |
| 5,389,305 | 2/1995 | Repinec et al. | 252/546 |
| 5,393,450 | 2/1995 | Shana'a | 252/170 |
| 5,415,810 | 5/1995 | Lee et al. | 252/545 |
| 5,449,475 | 9/1995 | Cauwet et al. | 252/174.23 |

FOREIGN PATENT DOCUMENTS

| | | |
|---|---|---|
| 0341071 | 11/1989 | European Pat. Off. |
| 9218100 | 10/1992 | WIPO |
| 9102 | 4/1994 | WIPO |
| 16042 | 7/1994 | WIPO |

OTHER PUBLICATIONS

Revista Italiana, 56, No. 10, Oct. 1974, Editor G. Fenaroli, G. Proserpio and G. Vianello Authors, English Translation.

*Primary Examiner*—Michael P. Tierney
*Attorney, Agent, or Firm*—Martin B. Barancik

[57] ABSTRACT

An aqueous liquid composition comprising of:
- a. about 4 to 10 wt % of anionic surfactant,
- b. about 1.5 to 5 wt % of a betaine,
- c. about 1.5 to 8 wt % of an alkyl polyglycoside wherein the average degree of polymerization is from about 1.1 to 6 and the average alkyl length is from about 8 to 14 carbon atoms, inclusive, and
- d. an antibacterial effective amount of an antibacterial agent or mixture of antibacterial agents.

3 Claims, No Drawings

MILD, AQUEOUS SKIN CLEANSING COMPOSITION

BACKGROUND OF THE INVENTION

This application is continuation in part of application Ser. No. 08/195,235, filed on Feb. 14, 1994, now abandoned.

There exists a continuing need for very mild skin cleansers. In addition, there exists a continuing need for skin cleansers which have an effective antibacterial activity. The addition of an antibacterial effect amount of an antibacterial agent to a very mild liquid composition can potentially bring about undesirable effects such as skin dryness and/or skin irritation. Although not necessarily present after infrequent use, the undesirable effects can manifest themselves after repeated washings. These undesirable characteristics have been addressed in a liquid cleansing composition which is ultra mild to the skin while providing effective antibacterial activity. Additional agents providing additional lather activity while essentially retaining the ultramildness can also be employed in the composition.

BRIEF SUMMARY OF THE INVENTION

In accordance with the invention there is an aqueous liquid composition comprising:

a. about 4 to 10 wt % of anionic surfactant, b. about 1.5 to 5 wt % of betaine, c. about 1.5 to 8 wt % of an alkyl polyglycoside wherein the average degree of polymerization is from about 1.1 to 6 and the average alkyl length is from about 8 to 14 carbon atoms, inclusive, and d. an antibacterial effective amount of an antibacterial agent or mixture of antibacterial agents.

Formulations of the invention have surprisingly been found to be unusually mild and provide effective antibacterial action in both in viva and in vitro test systems. In fact they are at least as mild if not actually milder than various commercial antibacterial liquid skin cleansing compositions on the market place such as Lever 2000 and Dial Liquid. Still further, they are unexpectedly as mild or milder than various non antibacterial liquid soaps such as Liquid Ivory Soap, Jergens Lotion Enriched Liquid Soap, Dove Beauty Wash and Clean and Smooth.

DETAILED DESCRIPTION OF THE INVENTION

The anionic surfactant which is employed in the aqueous liquid composition is any high foaming anionic surfactant such as a long chain sulfate, sulfonate, isethionate, carboxylate, taurate, sulfosuccinate, phosphate and the like. Alkoxylated, preferably ethoxylated materials are even more preferred. The most preferred material is an alkyl sulfate having an average of about 8 to 16 carbon atoms, preferably an average of 10 or 12 carbon atoms, most preferably normal alkyl. It is preferred that this material be ethoxylated with 1 to 4, preferably 2 or 3 average number of ethoxy groups. The cation is preferably an alkali metal or amine such as sodium, potassium or triethanolamine, most preferably sodium. The preferable anionic surfactant is sodium laureth sulfate with an average of 2 or 3 ethoxy groups. The anionic surfactant is present in the composition in quantities of from about 4 to 9 wt %, preferably about 5 to 8 wt % of the composition.

The second necessary component of the composition is a betaine. Various betaines are known and included in this composition but preferred are long chain alkyl carboxy amido alkylene betaines. The long chain alkyl group (including the acyl carbon) has an average of from about 8 to 18 carbon atoms, preferably 12 to 14 carbon atoms. The alkylene grouping between the amido group and the quaternary nitrogen atom of the betaine generally has from two to four carbon atoms, preferably three carbon atoms. The counterion can be any negative anion compatible with the betaine system. Preferred is cocoamido propylbetaine. The betaine is present in composition in from about 1.5 to 5wt %, preferably about 2 to 4.5 wt % of the composition.

The third essential component of the composition is an alkyl polyglycoside. The polyglycoside should have an average degree of polymerization of about 1.1 to 6, preferably about 1.3 to 1.8. The alkyl group has an average number of carbon atoms of about 8 to 16, preferably an average of about 10 to 12 carbon atoms. The alkyl group is preferably normal. These materials or available from such vendors as Henkel and Seppic. The alkylpolyglycoside is present in the composition in from about 2 to 8 wt %, preferably about 3 to 7 wt %.

The specific combinations of these three components seems to bring about an ultra mild to the skin cleansing composition even with the presence of the antibacterial agent therein.

The fourth component is an antibacterial agent present in quantities effective to inhibit the growth and/or kill bacteria on the skin. Although various known antibacterial agents can be employed such as chloroxylenol and the halogenated carbanilides, the preferred family of antibacterial agent is the halogenated phenoxy diphenyl ethers. The most preferred antibacterial agent is the specific diphenyl ether, Triclosan, 2,4,4'- trichloro - 2'- hydroxydiphenylether. This material is known to be effective against a large number of gram positive and gram negative bacteria. The preferred antibacterial agent is present in the composition in about 0.1 to about 1.5 wt %, preferably about 0.15 to 1.0 wt %.

Other agents may also be present in the composition, for example, additional nonpreferred anionic surfactants, thickeners, preservatives, dyes, and the like. Components which may also be present in the composition are the cationic polymers. These materials are known to provide good skin feel to skin cleansing compositions. It is preferable to have a skin feel effective amount of a cationic polymer in the composition. Quantities of cationic polymer of from about 0.01 to 0.1, preferably 0.02 to 0.04 wt % of the composition can be employed. Particularly preferred is the polymeric quaternium salt of acrylamide and dimethyl dialkyl ammonium chloride commonly known as Polyquaternium-7 and obtained from Calgon as Merquat 550, useful for skin feel. Additional anionic surfactant(s) which can be preferably present, particularly in combination with the laureth sulfate, are a taurate, an alkyl sulfosuccinate, a sulfoacetate, isethionate, alkylamidosulfo-succinate and the like.

The compositions are generally clear and white, preferably water white, in color. If a pearlescent composition is desired, opacifying agents such as glycol stearate, glycol distearate and styrene/acrylate copolymer can be added.

The compositions are formulated in the conventional manner. Below are formulations of the invention. These formulations are intended to exemplify the invention and not unduly limit the invention. All wt % are with reference to the final composition.

These formulations are prepared in the following manner. The surfactant system of laureth sulfate, betaine and alkylpolyglycoside are combined with water, a chelating agent (EDTA, 0.05 wt %), and an emollient such as Cetiol HE (PEG-7 Glyceryl Cocoate, 0.01 wt %) at room temperature (Part I). The Triclosan (trichloro hydroxy diphenyl ether) and a nonionic thickener such as PEG-120 methyl glucose dioleate, 0.2 wt %, are added to Part 1 (Part II). These are mixed and together heated 65°–70°C. The Polyquaternium-7, 0.04 wt % active, (Part III) is then added to Part I and Part II at the elevated temperature and cooling begins. A preservative and fragrance are then added to the cooled batch. A pH adjuster such as citric acid (0.1 wt %) and a viscosity adjuster such as sodium chloride are added to the batch. All these latter materials are common to cleansing formulations and form no part of the invention.

| Formulations - Wt % | | | |
|---|---|---|---|
| | I | II | III |
| Sodium laureth sulfate, 2 ethoxy (SLES) | 5.6 | 6.2 | 6.2 |
| Cocoamidopropylbetaine (CAMP) | 3.6 | 3.2 | 2.6 |
| alkyl (decyl) polyglycoside | 5.0 | 4.5 | 6.0 | average dp = 1.4 (APG)

Triclosan at the level of 0.2 wt % was present in all the compositions. Formulation I was tested in a number of in vitro and in vivo test systems for various characteristics such as mildness and anti-bacterial efficacy. Parameters evaluated include; skin barrier damage, erythema, edema, dryness, irritation potential, sensitization potential/hypoallergenicity and antibacterial efficacy.

Antibacterial efficacy of the formulation was tested using a zone of inhibition in vitro test system against staph aureus ATCC 27217 and 6538. The formulation demonstrated antibacterial efficacy.

A further in vitro antibacterial test system was employed, a short interval kill time test, to show the efficacy of the formulation against a gram negative bacteria, E. coli. This method is designed to determine the in vitro antimicrobial activity of a formulation during short exposure times.

In this method, test solutions are mixed with bacterial inoculum for one minute, after which the test system is neutralized and surviving bacteria enumerated. The formulation was effective.

Various in vivo test systems were employed to demonstrate anti-bacterial efficacy of the formulation. The hand imprint technique was used to demonstrate the residual activity of the formulation on the skin after a single wash versus a placebo liquid soap. Effectiveness was measured by the area of bacterial clearing (growth inhibition) on agar plates streaked with bacteria produced by contact with a hand washed with a test product. The organism used was a common Gram positive pathogen, (S. aureus). The area of clearing was measured using Image Analysis.

Results confirmed that the active ingredient in the formulation, Triclosan, is substantive to the skin, resulting in residual germ-fighting activity. The formulation of the invention is significantly more effective than the placebo liquid soap at inhibiting bacterial growth.

A further in vivo test employed was the Agar Patch Test. This test was used to compare the residual bacteriostatic activity of the formulation against E. Coli. versus a placebo liquid soap by determining the number of surviving bacteria on bacteria-streaked agar patches pressed against the volar surfaces of the forearms of panelists.

Fourteen volunteers participated in this study. After undergoing a one-week washout period in which the panelists refrained from using any antibacterial products such as soaps, shampoos, lotions, etc., the panelists washed their forearms for 60 seconds with either the test product or the placebo. After the arms air-dried, bacteria-streaked agar plates, in triplicate, were placed against the forearms and held securely with adhesive tape. The agar plates were removed after a contact time of 30 minutes and the panelists forearms were disinfected with 70% ethanol.

Results show that skin washed with the formulation is significantly better in inhibiting the growth of E. Coli.

The mildness of the formulation was verified in a series of test systems, in vitro and in vivo.

The Collagen Swelling Test compares the tendency of products to affect the protein structure in a strip of collagen. This effect is directly related to the irritation potential of the product. SLS (Sodium lauryl sulfate), a known harsh anionic surfactant and water were used as controls. The formulation is significantly milder than antibacterial Lever 2000® Liquid and SLS in this test system.

The zein test method utilizes the concept that zein is a protein insoluble in aqueous solutions unless denatured. Denaturation can occur through contact with irritating detergents. A premeasured quantity of zein is incubated for 1 hour, at room temperature, under agitation with a solution of the finished product at 1% of dry extract. After incubation, the solubilized zein is isolated and assayed. The more irritating the product, the more zein is solubilized. SLS (Sodium lauryl sulfate), a known harsh anionic surfactant and water are used as controls. The formulation is again significantly milder than antibacterial Lever 2000® Liquid and SLS.

The disruption of barrier property was determined by studying the increase in water permeation of tritiated water through pig skin, indicated by an increase in the water permeability constant ($K_p$). Two types of permeability experiments were performed: "patch test" conditions (single, long term exposure) and "exaggerated arm wash" conditions (multiple, short exposures). Results of a 24-hour "patch test" showed that the $K_p$ of skin treated with the formulation was significantly lower than Dial's antibacterial liquid and directionally lower than Lever 2000 AB Liquid. Results of two "exaggerated arm wash" studies were consistent in that the formulation was directionally less damaging to the skin barrier than Lever 2000® Antibacterial Liquid or Dial® Antibacterial Liquid.

An in vitro sebum assay showed that the formulation is not as defatting to the skin as the following competitive antibacterial liquids: Clean & Smooth®, Safeguard®, Dial®, Lever 2000® and Jergens®.

In this study, synthetic human sebum (triolein, oleic acid, cetyl palmitate and squalene) is deposited onto wool swatches from a solution spiked with C-14 oleic acid and H-3 squalene. An aliquot of a 50% antibacterial liquid (1:1 dilution with water) is added. After shaking for 1 minute, the swatches are filtered, rinsed and air-dried. A solvent is added to solubilize the residual sebum and radioactive label. The samples are then counted for residual oleic acid and squalene.

A Soap Chamber Test run by an independent testing laboratory evaluated the relative irritation potentials of the formulation versus Lever 2000® Liquid in a double blind manner.

The soap chamber test method used is the one of Simion et al (Contact Dermatitis, 25 (1991) 242–249).

Twenty five female panelists with a previous history of skin readily irritated by detergents were recruited for this study. Occlusive patches were applied to the panelists' volar forearms for two consecutive twenty four hour periods after which the test sites were evaluated for visual and instrumental measures of irritation.

The parameters evaluated were:

Erythema (redness)

Edema

Dryness—Clinically Observed

Transepidermal water loss (TEWL)

The test sits were evaluated for erythema (skin redness) instrumentally using a Minolta chromameter as well as by an expert observer. Instrumental measurements of transepidermal water loss, which is a measure of the barrier function of the stratum corneum, were made using the Servo Med Evaporimeter.

The formulation was found to be significantly milder than Lever 2000 for erythema, having significantly less erythema (clinically observed) at the 48 and 72 hour evaluation periods.

Additionally signficantly less stratum corneum barrier damage (TEWL) was observed at the 24 and 48 hour evaluation periods. Still further significantly less instrumentally measured redness was observed at the 48 hour evaluation period.

Subjects receiving an excessive erythema score (2 or greater) after the first 24 hour patch were not repatched. A low incidence of drop out after the first 24 hour patch relative to the other products tested again confirms the unusual mildness of the formulation.

With respect to in vivo activity, the aforementioned modified soap chamber test system mean erythema score and mean change in evaporimetry score demonstrated that the invention formulation was either as mild as or statistically significantly milder than the previously mentioned commerical liquid.

An exaggerated arm wash study was conducted to verify the superior clinical mildness of the formulation under more realistic exposure conditions. This study compared the formulation to Lever 2000® Antibacterial Liquid soap. Skin response was evaluated using Clinical observations (dryness/erythema)

Instrumental measurements (colorimetry/evaporimetry)

Panelist self-evaluations

Thirty-two female volunteers with a history of skin readily irritated by surfactants participated in this study. A pre-conditioning period required the panelists to use Dove Beauty Bar instead of their normal soap for 2 weeks prior to the study. The forearm of each panelist was washed with one of the test products for two minutes, four times a day for four days and two times on the fifth day.

The skin of each panelist was evaluated before the first wash of the study by observer scoring, self-evaluation, and instrumental measurements. (instrumental measurements were made using the Minolta Chroma Meter and the Servo Med Evaporimeter.) Before each wash, both observer scoring and self evaluations were performed. Besides the initial evaluation, instrumental measurements were taken three hours after each panelist's final wash. The measurements were made following a 30 minute acclimation period in a controlled environment room (constant humidity/temperature).

The results of this study show that the formulation is superior to Lever 2000 Antibacterial Liquid Soap based on clinically observed erythema and dryness.

Statistical evaluation of endpoint dryness and erythema scores show that the formulation induced statistically less dryness ($p=0.03$) and erythema ($p=0.007$) than Lever 2000 Antibacterial Liquid.

Instrumental measurements confirmed that the formulation induced directionally less skin redness and transepidermal water loss than Lever 2000 antibacterial liquid.

The panelist's self-assessments also showed that the formulation was more frequently more favorably rated than Lever 2000 Antibacterial Liquid soap.

Two hundred panelists participated in a repeat insult patch test for irritation and sensitization potential of the formulation. The induction phase consisted of 9 occlusive patch applications of 5% aqueous solutions of test material over 3 consecutive weeks. Each site was scored 24–48 hours after patch removal. Two weeks following induction, challenge patches were applied to previously unpatched sites. Patches were removed 24 hours after application and the challenge sites were scored 24 hours after application. This study was completed under the supervision of a Board Certified Dermatologist.

Results of the test indicate that the formulation does not cause sensitization or allergic reactions.

Formulations II and III were tested for mildness in the aforementioned collagen swelling test and were found to be at least as mild as antibacterial Lever 2000 Liquid. Below is a further formulation.

| Formulation IV | Wt % |
| --- | --- |
| SLES (3 ethoxy) | 8.6 |
| CAMP | 4.2 |
| APG (Decyl) (1.6 DP) | 1.5 |
| Triclosan | 0.2 |

The above-identified antibacterial formulation of the invention was tested for in vitro mildness in the aforementioned collagen swelling test and the zein test (½ dilution) as well as a pH—rise test against various commercial liquid cleansing compositions not having an antibacterial agent therein. These compositons were Liquid Ivory Soap, Jergens Lotion Enriched Liquid Soap, Dove Beauty Wash and Clean & Smooth. The invention formulation was statistically significantly milder than all of the commercial non-antibacterial liquids in the collagen swelling test system and Zein test system. In the pH rise test system it was statistically significantly milder than all the commercial liquids except for Clean & Smooth wherein the invention formulation was directionally milder.

We claim:

1. An aqueous mild to the skin cleansing composition comprising a. about 4 to 10 wt. % of a laureth sulfate having an average of one to four ethoxy groups, b. about 1.5 to a maximum of 5 wt. % of an alkyl carboxy amido alkylene betaine wherein alkyl is about 8 to 18 carbon atoms and alkylene is from two to four carbon atoms, c. about 1.5 to 8 wt. % of an alkyl polyglycoside wherein the average degree of polymerization is from about 1.3 to 1.8 and d. an antibacterial effective mount of triclosan.

2. The composition in accordance with claim 1 wherein a is a sulfate with an average of 2 to 3 ethoxy groups.

3. The composition in accordance with claim 1 wherein the betaine has an alkyl group with 10 to 12 carbon atoms.

* * * * *